US012791549B2

(12) United States Patent
Qahtani et al.

(10) Patent No.: US 12,791,549 B2
(45) Date of Patent: Nov. 10, 2026

(54) APPROACH TO DETERMINE WATER CUT IN OIL AND GAS PROCESS FACILITY

(71) Applicant: SAUDI ARABIAN OIL COMPANY, Dhahran (SA)

(72) Inventors: AbdulRahman M. Qahtani, Dhahran (SA); Mutlaq F. Azmi, As Saffaniyah (SA); Said S. Jaroudi, Saihat (SA); Naif M. Alghuthayf, Dammam (SA); Mohammed A. Alswayied, Riyadh (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 354 days.

(21) Appl. No.: 18/746,761

(22) Filed: Jun. 18, 2024

(65) Prior Publication Data

US 2025/0383337 A1 Dec. 18, 2025

(51) Int. Cl.
*G01N 33/28* (2006.01)
*G01N 9/36* (2006.01)

(52) U.S. Cl.
CPC .......... *G01N 33/2847* (2013.01); *G01N 9/36* (2013.01); *G01N 33/2823* (2013.01)

(58) Field of Classification Search
CPC ... G01N 33/2847; G01N 9/36; G01N 33/2823
See application file for complete search history.

(56) References Cited

U.S. PATENT DOCUMENTS

| | | | |
|---|---|---|---|
| 8,788,209 B2 | 7/2014 | Foot et al. | |
| 10,794,847 B2 | 10/2020 | Black et al. | |
| 2022/0380688 A1* | 12/2022 | Soliman | G05D 9/12 |

OTHER PUBLICATIONS

Falke, "How to Measure and Plot Pump Flow", Mar. 2021, https://www.thedigitaltransformationacademy.com/wp-content/uploads/2021/03/How-to-Measure-and-Plot-Pump-Flow.pdf (Year: 2021).*
Drilling Formulas.com,"Determine the density of oil and water mixture", 2009, https://www.drillingformulas.com/determine-the-density-of-oil-and-water-mixture/ (Year: 2009).*
Fetoui, "Specific Gravity & API Gravity", 2018, https://production-technology.org/specific-gravity-api-gravity/) (Year: 2018).*

(Continued)

*Primary Examiner* — Allen C Chein
(74) *Attorney, Agent, or Firm* — Osha Bergman Watanabe & Burton LLP

(57) ABSTRACT

Processes, systems, and methods for determining water cut of a fluid sample in an oil and gas process facility including obtaining the fluid sample in a degassing vessel, measuring a pump suction pressure, a pump discharge pressure, a flow rate, and a temperature of the fluid sample, and obtaining a pump curve corresponding to the pump, the pump curve showing a relationship between the flow rate and a pump head. Processes, systems, and methods for determining water cut also include receiving the pump suction pressure, the pump discharge pressure, the flow rate, and the temperature, determining the pump head corresponding to the flow rate, determining a specific gravity of the fluid sample by Equation 1, and determining a water cut of the fluid sample by Equations 2 and 3, using a computer processing unit.

20 Claims, 6 Drawing Sheets

(56) References Cited

OTHER PUBLICATIONS

Pumpfundamentals, "Pressure or head", 2016, https://www.pumpfundamentals.com/pressure_and_static_head.htm) (Year: 2016).*
Correction Table for Specific Gravity Hydrometers 60° F/60° F (15.56° C/15.56° C), 2023, https://thermcoproducts.com/wp-content/uploads/2023/04/Correction-Table-for-Specific-Gravity-Hydrometers-1.pdf (Year: 2023).*

* cited by examiner

APPROACH TO DETERMINE WATER CUT IN OIL AND GAS PROCESS FACILITY

BACKGROUND

Devices for measuring individual flow rates of fluids in a produced fluids mixture are commonly used in oilfield operations. Knowledge of the individual fluid flow rates allows for reservoir management, production allocation, operational control, and field development. Accurate flow rate measurement of produced fluids such as oil and gas are therefore important for maximizing production and minimizing cost in oil and gas operations.

Water cut is a key indicator of the overall quality and productivity of an oil well or reservoir which provides valuable insights into the behavior and characteristics of the reservoir as well as the quality of product oil and gas. The water cut parameter is one of the most important factors in determining crude oil quality. It is the ratio of water produced compared to the volume of total liquids produced from an oil well. The water cut content in crude oil can have a negative impact on the value and profitability of an oil well. A high water cut can lead to reduced oil recovery due to reservoir pressure decline and increased operating costs associated with water separation, treatment, and disposal.

Conventional methods to determine the water cut is based on the water cut flow meter. Current measurement techniques may require frequent calibrations and maintenance, large operation space, costly monitoring for corrosion and safety, and specialized equipment. In addition, current methods used to measure flow rates of produced fluids may be inaccurate in high water cut or high gas to oil ratio wells.

Accordingly, there exists a need for more accurate systems and methods to measure water cut in oil and gas applications.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a process for determining water cut of a fluid sample in an oil and gas process facility, including a degassing vessel. The degassing vessel includes an inlet line, fluidly connected to and entering the degassing vessel, a gas outlet line and a liquid outlet line, both fluidly connected to and exiting the degassing vessel, a pump suction pressure transmitter disposed on the liquid outlet line configured to measure a pump suction pressure, a pump discharge pressure transmitter disposed on the liquid outlet line configured to measure a pump discharge pressure, a flow transmitter disposed on the liquid outlet line configured to measure a flow rate, and a temperature transmitter, configured to measure a temperature, disposed on the liquid outlet line, a pump fluidly connected to the degassing vessel via the liquid outlet line. The process also includes a computer processing unit, coupled to the degassing vessel, the pump suction pressure transmitter, the pump discharge pressure transmitter, the flow transmitter, and the temperature transmitter, the computer processing unit having a memory and processor, the memory storing instructions that, when executed by the processor, cause the processor to measure the pump suction pressure of the fluid sample in the degassing vessel, the pump discharge pressure of the fluid sample, the flow rate of the fluid sample, and the temperature of the fluid sample, obtain a pump curve corresponding to the pump, the pump curve showing a relationship between the flow rate and a pump head, receive the pump suction pressure, the pump discharge pressure, the flow rate, and the temperature, determine the pump head corresponding to the flow rate received by the computer processing unit, determine a specific gravity of the fluid sample by Equation 1, and determine a water cut of the fluid sample by Equations 2 and 3.

In another aspect, embodiments disclosed herein relate to a method for determining water cut of a fluid sample in an oil and gas process facility, including obtaining the fluid sample in a degassing vessel by an inlet line, fluidly connected to and entering the degassing vessel, measuring a pump suction pressure of the fluid sample using a pump suction pressure transmitter disposed on a liquid outlet line at an upstream location from a pump, measuring a pump discharge pressure of the fluid sample using a pump discharge pressure transmitter disposed on the liquid outlet line, measuring a flow rate of the fluid sample using a flow transmitter disposed on the liquid outlet line, and measuring a temperature of the fluid sample using a temperature transmitter disposed on the liquid outlet line, where the liquid outlet line is fluidly connected with and exiting the degassing vessel, and where the pump discharge pressure transmitter, the flow transmitter, and the temperature transmitter in-line with each other at a downstream location from the pump. The method also includes obtaining a pump curve corresponding to the pump, the pump curve showing a relationship between the flow rate and a pump head, receiving, with a computer processing unit, the pump suction pressure, the pump discharge pressure, the flow rate, and the temperature, where the computer processing unit is coupled to the degassing vessel, the pump suction pressure transmitter, the pump discharge pressure transmitter, the flow transmitter, and the temperature transmitter. The method further includes determining, with the computer processing unit, the pump head corresponding to the flow rate received by the computer processing unit, determining, with the computer processing unit, a specific gravity of the fluid sample by Equation 1, and determining, with the computer processing unit, a water cut of the fluid sample by Equations 2 and 3.

In yet another aspect, embodiments disclosed herein relate to a system for determining water cut of a fluid sample in an oil and gas process facility, including a degassing vessel, the degassing vessel including, an inlet line, fluidly connected to and entering the degassing vessel, a gas outlet line and a liquid outlet line, both fluidly connected to and exiting the degassing vessel, a pump suction pressure transmitter disposed on the liquid outlet line configured to measure a pump suction pressure, a pump discharge pressure transmitter disposed on the liquid outlet line configured to measure a pump discharge pressure, a flow transmitter disposed on the liquid outlet line configured to measure a flow rate, and a temperature transmitter disposed on the liquid outlet line configured to measure a temperature. The system also includes a pump, fluidly connected to the degassing vessel via the liquid outlet line, a reservoir fluidly connected to an upstream side of the degassing vessel by the inlet line, a downstream process line fluidly connected to a downstream side of the degassing vessel and to the reservoir, and a computer processing unit, coupled to the degassing vessel, the pump suction pressure transmitter, the pump discharge pressure transmitter, the flow transmitter, and the temperature transmitter, the computer processing unit having a memory and processor, the memory storing instructions that, when executed by the processor, cause the processor to measure the pump suction pressure of the fluid sample in the degassing vessel, measure the pump discharge pressure of the fluid sample, measure the flow rate of the fluid sample, measure the temperature of the fluid sample, obtain a pump curve corresponding to the pump, the pump curve showing a relationship between the flow rate and a pump head. The computer processing unit is also configured to receive the pump suction pressure, the pump discharge pressure, the flow rate, and the temperature, determine the pump head corresponding to the flow rate received by the computer processing unit, determine a specific gravity of the fluid sample by Equation 1 and determine a water cut of the fluid sample by Equations 2 and 3.

Other aspects and advantages of the claimed subject matter will be apparent from the following description and the appended claims.

BRIEF DESCRIPTION OF DRAWINGS

In the FIGURES, the same reference numeral may be used to indicate process equipment as well as the material or component contained within the equipment.

DETAILED DESCRIPTION

Figure 1:
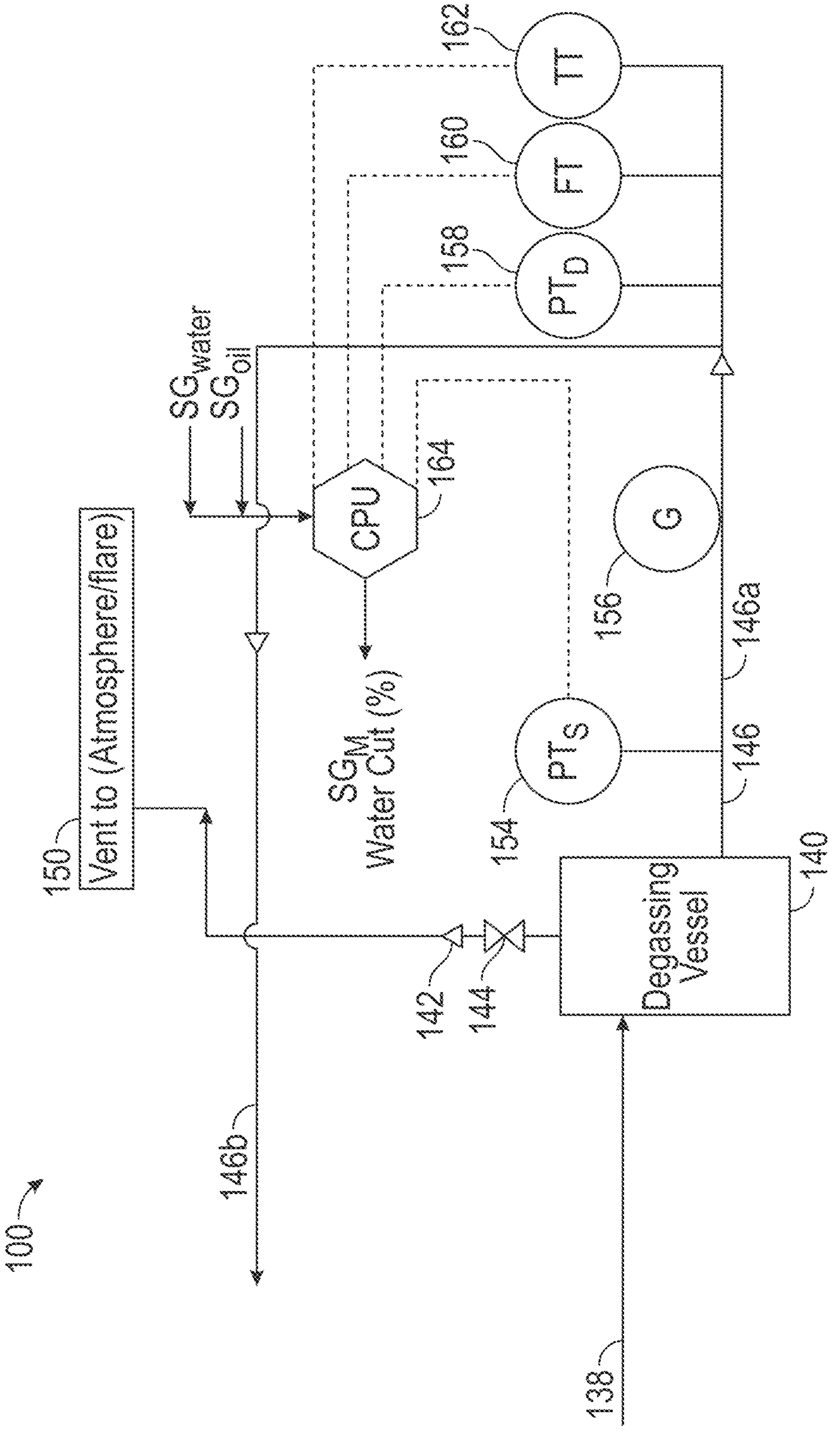
FIG. 1 illustrates a process for determining water cut according to one or more embodiments.

Throughout the application, ordinal numbers (for example, first, second, third) may be used as an adjective for an element (that is, any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a fluid sample" includes reference to one or more of such samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope of the invention should not be considered limited to the specific arrangement of steps shown in the flowcharts.

Although multiply dependent claims are not introduced, it would be apparent to one of ordinary skill that the subject matter of the dependent claims of one or more embodiments may be combined with other dependent claims.

Embodiments disclosed herein generally relate to systems and methods for determining water cut of a fluid sample based on density calculations while utilizing a system that can be connected to the well head platforms or at the inlet manifold for any wet crude handling facility. Systems and methods described herein may also be used for various applications to determine the water cut for any liquid mixture, and examples described in the following sections shall not be taken as limiting.

In some embodiments, systems and methods described herein may be connected to unmanned well head platforms, at the manifold for any wet crude handling facility, or any similar application involving a flow of three phases. In said instances, a small three phases flow portion from the reservoir line can be directed and used as input for the new design system according to embodiments described herein. In some embodiments, the flow will be degassed by the degassing vessel, where the gas is separated and vented out either to atmosphere or to be compressed back to the flow line. In some embodiments, the remaining mixture which may be oil and water, will be directed to a centrifugal pump equipped with pressure, flow, and temperature transmitters. Utilizing operational parameters obtained from the pressure, flow, and temperature transmitters along with the pump curve data, may allow for a mixture specific gravity to be computed and determined.

Systems for Determining Water Cut

One or more embodiments relate to systems for determining water cut of a fluid sample in an oil and gas process facility. Systems of one or more embodiments include a degassing vessel, a centrifugal pump, flow and temperature transmitters, and a central processing unit. In some embodiments, the system may also include a gas compressor.

FIG. 1 depicts a process 100 for determining water cut according to one or more embodiments. The process 100 includes a degassing vessel 140, a pump 156, and a central processing unit 164.

In one or more embodiments, an inlet line 138 enters the degassing vessel 140 and a liquid outlet line 146 and gas outlet line 142 exit the degassing vessel 140. An inlet stream may flow through the inlet line 138, a liquid stream **146*a* may flow through the liquid outlet line 146, and a gas stream may flow through the gas outlet line 142**.

As non-limiting examples, the inlet stream 138 may originate from an oil and gas reservoir or any wet crude processing facility. Accordingly, the inlet stream 138 may contain any components associated with oil and gas or wet crude processing, including but not limited to oil and other hydrocarbons, water, natural gas and other dissolved gases including but not limited to hydrogen sulfide ($H_2S$) and carbon dioxide ($CO_2$), dissolved solids, and the like. As would be understood by one of ordinary skill in the art, compositions of the inlet stream 138 may vary based on many factors including geological location, reservoir characteristics (rock types, temperatures, depths, pressure), and the like. However, the inlet stream 138 in the process 100 of one or more embodiments may contain primarily oil, water, and gas.

The inlet stream may have an oil concentration which is a majority of the inlet stream composition. The inlet stream may have an oil concentration in a range of from about 0 to about 100 wt %. For example, the inlet stream may have an oil concentration in a range having a lower limit of from about 0.4, 1, 5, 10, and 25 wt % to an upper limit of about 50, 75, 90, and 100 wt %, where any lower limit may be paired with any upper limit.

The inlet stream may have a water concentration which is a substantial portion of the inlet stream composition. The inlet stream may have a water concentration in a range of from about 0 to about 100 wt %. For example, the inlet stream may have a water concentration in a range having a lower limit of from about 0.4, 1, 5, 10, and 25 wt % to an upper limit of about 50, 75, 90, 100 wt %, where any lower limit may be paired with any upper limit.

Returning to FIG. 1, the degassing vessel 140 may separate a fluid sample entering the degassing vessel 140 by the inlet stream 138, into liquid and gas components, i.e., the liquid stream 146*a* and the gas stream 142. In one or more embodiments, the gas stream 142 may be vented to the atmosphere and/or flared 150. In some embodiments, the gas stream 142 may be recycled into additional upstream or downstream processes (not shown) which will be shown and discussed in FIGS. 2 and 3, below. A gas flow control system 144 may be disposed on the gas outlet line 142 and may be used to control the flow of the gas stream 142 either to the atmosphere 150 or otherwise.

The degassing vessel of one or more embodiments may be any suitable degasser capable of removing and separating entrained and dissolved gases from a stream, such as the inlet stream, described above. For example, the degassing vessel may be a vacuum tank degasser, an atmospheric degasser, a produced water degasser, or the like.

The liquid stream of one or more embodiments may contain primarily oil and water. The concentrations of oil and water contained in the liquid stream may be the same as those in the inlet stream from which it originates.

The gas stream of one or more embodiments may include natural gas and other dissolved gases, including but not limited to hydrogen sulfide ($H_2S$) and carbon dioxide ($CO_2$). The concentrations of natural gas and other dissolved gases contained in the gas stream may be the same as those in the inlet stream from which it originates.

The gas flow control system of one or more embodiments may contain operable valves to control flow, release gases, etc. but may also include emergency release lines in case a high pressure slug is received. For example, a burst disc, pressure relief valve, etc. may be used for safety reasons to prevent build-up of high pressure in the sample vessel. While not explicitly shown in the drawings, one of ordinary skill in the art will recognize the inclusion of elements described herein.

Keeping with FIG. 1, the liquid stream 146*a* may flow through a pump 156 in line with the liquid outlet line 146, where the pump 156 is fluidly connected to the degassing vessel via the liquid outlet line 146. Upon flowing through the pump 156, the liquid stream 146*a* becomes pressurized to produce a pressurized liquid stream 146*b*.

The pump of one or more embodiments may be any suitable pump configured to pressurize a liquid stream known in the art. For example, the pump may be a radial centrifugal pump or an axial centrifugal pump.

Figure 6:
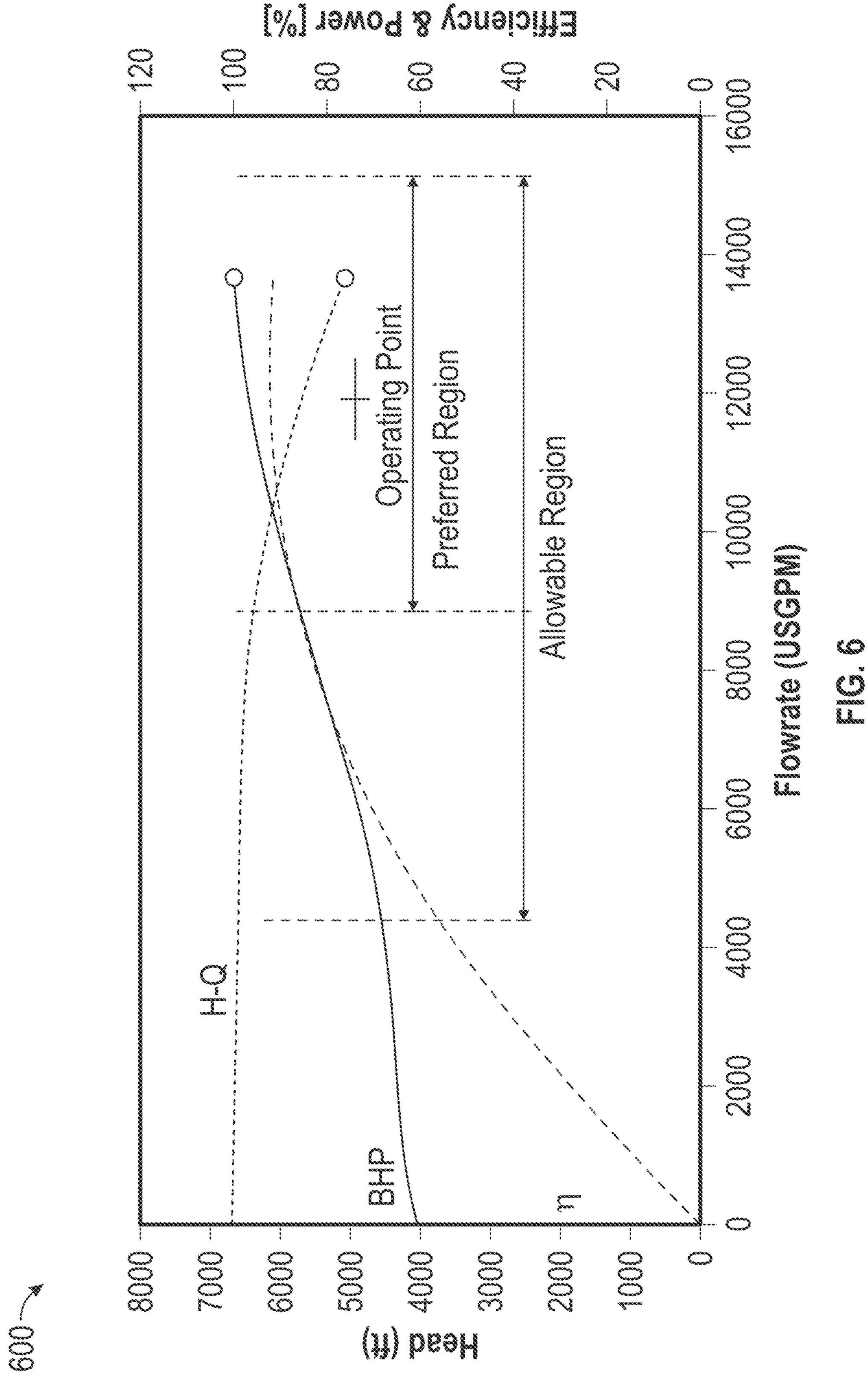
FIG. 6 shows an example pump curve according to one or more embodiments.

The pump of one or more embodiments may be associated with one or more pump curves. A "pump curve," also known as a "pump performance curve," is a measurement of the performance of a pump and is defined herein as a relationship between how a pump will perform in regard to pressure head and flow. Pump curves are defined for a specific operating speed (rpm) and a specific inlet/outlet diameter for a specific operating speed (rpm) and a specific inlet/outlet diameter. The pump curve of one or more embodiments may be used in the method of one or more embodiments, along with other acquired parameters, to determine a mixture specific gravity. An example pump curve is shown in FIG. 6 and will be described in more detail below.

In one or more embodiments, a pump curve associated with the pump 156 may be used to determine a pump head based on a flow rate measured from the flow transmitter 160. For example, a fluid sample may enter the degassing vessel 140 and be separated into the liquid stream 146*a* and the gas stream 142*a*. The liquid stream 146*a* may then pass through the pump 156 and be pressurized to produce the pressurized liquid stream 146*b*. A flow rate of the pressurized liquid stream 146*b* may be measured by the flow transmitter 160. The measured flow rate may then be used to determine a corresponding pump head from the pump curve associated with the pump 156.

The pressurized liquid stream of one or more embodiments may have a pressure in a range of from 20 to 700 psi. For example, the pressure of the pressurized liquid stream may be in a range having a lower limit of from about 20, 50, 100, and 200 psi to an upper limit of about 250, 500, and 700 psi, where any lower limit may be paired with any upper limit.

The pressurized liquid stream may include any of the components of the liquid stream from which it originates.

In the process 100 of FIG. 1, a pump suction pressure transmitter 154 configured to measure a pump suction pressure may be disposed on the liquid outlet line 146 at a location which is upstream from the pump 156. A pump discharge pressure transmitter 158 configured to measure a pump discharge pressure may be disposed on the liquid outlet line 146 at a location which is downstream from the pump. A flow transmitter 160 configured to measure a flow rate and a temperature transmitter 162 configured to measure a temperature may also be located on the liquid outlet line 146 at a downstream location from the pump 156. The location of the flow transmitter 160, the pump discharge pressure transmitter 158, and the temperature transmitter 162 relative to each other is arbitrary, provided the pump discharge pressure transmitter 158, the flow transmitter 160, and the temperature transmitter 162 are located in-line with one another downstream of the pump 156.

The pump suction pressure transmitter and the pump discharge pressure transmitter of one or more embodiments includes any pressure gauge known in the art configured to measure a pressure value. The pressure gauge may be mechanical, such as an analog type pressure gauge. Examples of analog pressure gauges include a bourdon tube and a diaphragm or bellows. The pressure gauge may also be digital and may operate using a strain gauge, piezoelectrics, and the like. The measurement device used as the pressure gauge may be local or may include a transmitter to relay a signal indicative of the measurement to a remote location.

The flow transmitter of one or more embodiments may include any flow transmitter known in the art configured to measure and control a flow rate. In one or more embodiments, the flow transmitter may include an automatic flow control valve which is configured to receive instructions related to adjust a flow rate, for example, from a computer system, and may be automatically operated to adjust the flow rate of a fluid stream according to the received instructions. In one or more embodiments, the flow control valve may be manually operated. A flow control valve may also be referred to as a flow regulator or flow controller, and these terms are to be understood according to one or more embodiments as referring to the same device. The flow control valve of one or more embodiments may include, for example, a ball valve, a check valve, a butterfly valve, a globe valve, a gate valve, a needle valve, and combinations therein. The flow transmitter of one or more embodiments may include any suitable flow ratio controller known in the art. The flow control valve may include a valve, or the flow control valve may be a flow control system, which may include both a flow control valve and a flow ratio controller and/or transmitter configured to operate the flow control valve based on instructions received from a central processing unit.

The temperature transmitter of one or more embodiments may include any temperature transmitter known in the art configured to measure a temperature value. For example, the temperature transmitter may be a temperature gauge including a contact thermometer and may be coupled with a probe or thermistor. The temperature gauge may be a digital thermometer, an analogue thermometer, a probe thermometer, a thermocouple, a thermistor, a resistance temperature detector, an infrared sensor, or the like. The measurement device used as the temperature gauge may be local or may include a transmitter to relay a signal indicative of the measurement to a remote location.

The process 100 of FIG. 1 may also include a central processing unit 164. In one or more embodiments, the central processing unit 164 is in electrical communication with each of the pump suction pressure transmitter 154, the pump discharge pressure transmitter 158, the flow transmitter 160, and the temperature transmitter disposed on the liquid outlet line 146.

In one or more embodiments, the central processing unit 164 may be coupled to the degassing vessel, the pump suction pressure transmitter 154, the pump discharge pressure transmitter 158, the flow transmitter 160, and the temperature transmitter 162. The central processing unit 164 may be configured to receive a suction pressure from the pump suction pressure transmitter 154. The central processing unit 164 may also be configured to receive a discharge pressure from the pump discharge pressure transmitter 158. The central processing unit 164 may also be configured to receive a flowrate from the flow transmitter 160. The central processing unit 164 may be configured to receive a temperature from the temperature transmitter 162. In one or more embodiments, the central processing unit 164 may also be configured to receive other input parameters, including but not limited to a specific gravity of water and a specific gravity of oil. In one or more embodiments, the central processing unit may be configured to provide output parameters to a user interface, including but not limited to a specific gravity of the pressurized liquid stream **146*b*, a ratio of water content of the pressurized liquid stream 146*b*, and a water cut percentage of the pressurized liquid stream 146*b*. Electrical communication is depicted by dashed lines in FIG. 1**.

Figure 5:
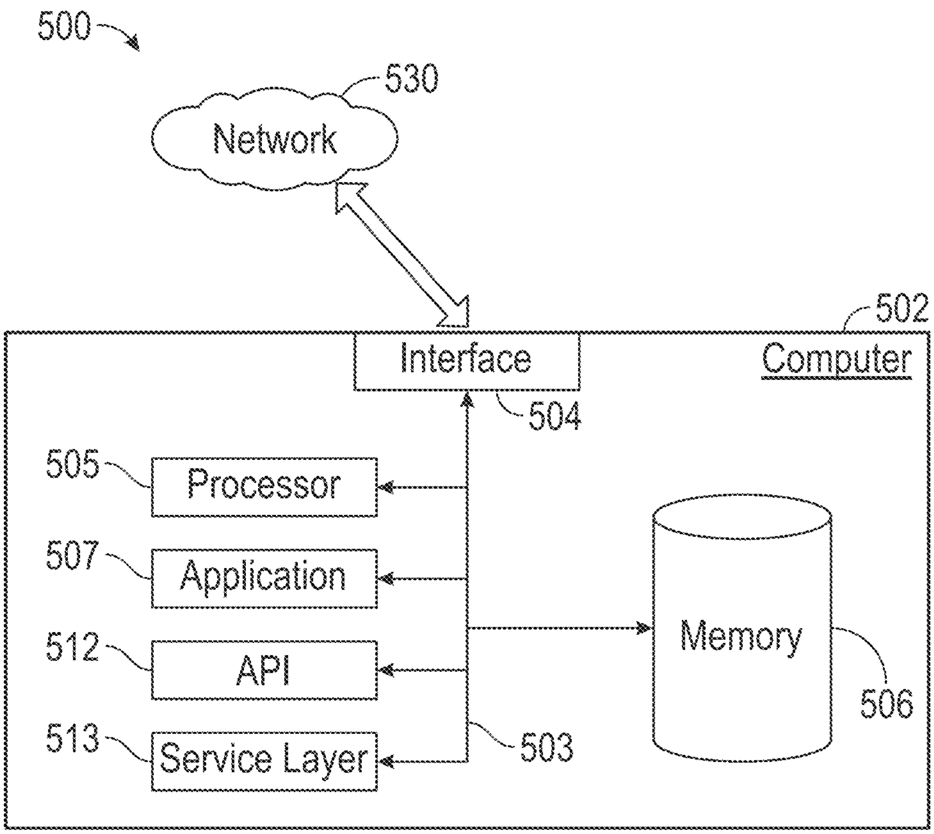
FIG. 5 is an example computer system according to one or more embodiments.

The central processing unit 164 of one or more embodiments may be a computer such as the computer shown in FIG. 5. In one or more embodiments, the central processing unit 164 may also be configured to carry out methods according to one or more embodiments. The methods of one or more embodiments will be discussed in more detail in the following sections.

Figure 2:
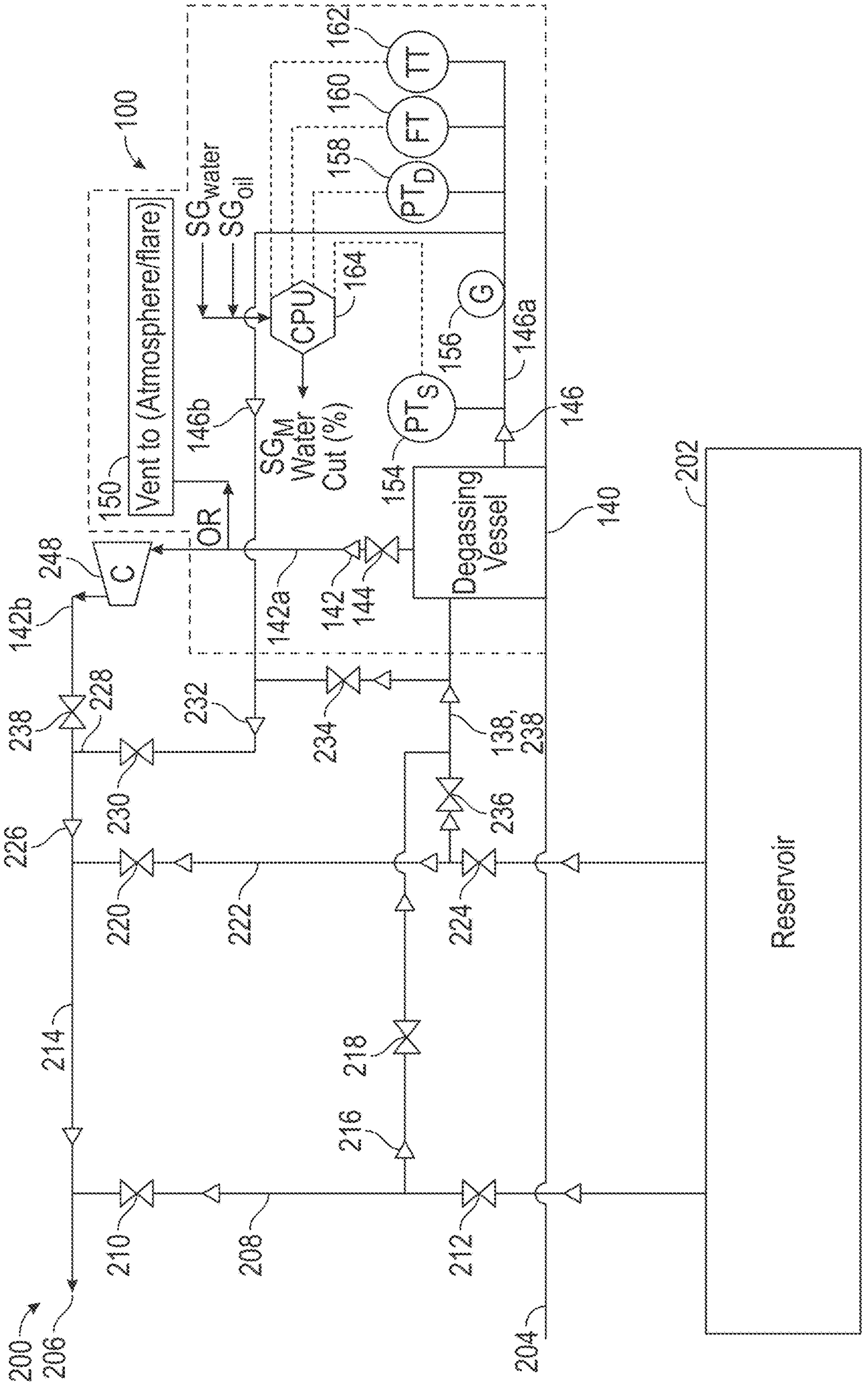
FIG. 2 illustrates a first system for determining water cut according to one or more embodiments.

FIG. 2 illustrates a first system for determining water cut according to one or more embodiments. The system 200 of FIG. 2 may include the process 100 of FIG. 1, a reservoir 202, and a downstream process line 214.

In one or more embodiments, the system 200 includes the process 100 of FIG. 1, including all of the elements as described with regard to FIG. 1, above. For example, the system 200 may include a degassing vessel 140, a pump 156, and a central processing unit 164. The system 200 may also include an inlet line 138 entering the degassing vessel 140 and a liquid outlet line 146 and gas outlet line 142 exiting the degassing vessel 140. A second inlet stream 238 may flow through the inlet line 138, a liquid stream **146*a* may flow through the liquid outlet line 146, and a gas stream 142*a* may flow through the gas outlet line 142. The degassing vessel 140 may separate a fluid sample entering the degassing vessel 140 by the second inlet stream 238, into liquid and gas components, i.e., the liquid stream 146*a* and the gas stream 142*a***.

The degassing vessel of one or more embodiments may be any degassing vessel as described in FIG. 1, above. The gas flow control system of one or more embodiments may be any gas flow control system as described in FIG. 1, above.

The second inlet stream 238 in FIG. 2 may originate from a reservoir 202. Accordingly, the second inlet stream 238 may contain any components associated with an oil and gas reservoir including but not limited to oil and other hydrocarbons, water, natural gas and other dissolved gases including but not limited to hydrogen sulfide ($H_2S$) and carbon dioxide ($CO_2$), dissolved solids, and the like. As would be understood by one of ordinary skill in the art, compositions of the second inlet stream 238 may vary based on many factors including geological location, reservoir characteristics (rock types, temperatures, depths, pressure), and the like. However, the second inlet stream 238 in the system 200 of one or more embodiments may contain primarily oil, water, and gas.

The liquid stream of one or more embodiments may contain primarily oil and water. The concentrations of oil and water contained in the liquid stream may be the same as those in the second inlet stream from which it originates. Compositions of the liquid stream may be the same as those described with regard to FIG. 1, above.

The gas stream of one or more embodiments may include natural gas and other dissolved gases, including but not limited to hydrogen sulfide ($H_2S$) and carbon dioxide ($CO_2$). The concentrations of natural gas and other dissolved gases contained in the gas stream may be the same as those in the inlet stream from which it originates. Compositions of the gas stream may be the same as those described with regard to FIG. 1, above.

Keeping with FIG. 2, in the system 200, the liquid stream **146*a* may flow through a pump 156 in line with the liquid outlet line 146, where the pump 156 is fluidly connected to the degassing vessel via the liquid outlet line 146. Upon flowing through the pump 156, the liquid stream 146*a* becomes pressurized to produce a pressurized liquid stream 146*b***.

The pump of one or more embodiments may be any suitable pump as described in FIG. 1, above. As previously described, the pump of one or more embodiments may be associated with one or more pump curves.

In one or more embodiments, a pump curve associated with the pump 156 may be used to determine a pump head based on a flow rate measured from the flow transmitter 160, as described above. The measured flow rate may then be used to determine a corresponding pump head from the pump curve associated with the pump 156.

The pressurized liquid stream of one or more embodiments may have a pressure and composition as described in regard to FIG. 1, above.

In the system 200 of FIG. 2, a pump suction pressure transmitter 154 configured to measure a pump suction pressure may be disposed on the liquid outlet line 146 at a location which is upstream from the pump 156. A pump discharge pressure transmitter 158 configured to measure a pump discharge pressure may be disposed on the liquid outlet line 146 at a location which is downstream from the pump. A flow transmitter 160 configured to measure a flow rate and a temperature transmitter 162 configured to measure a temperature may also be located on the liquid outlet line 146 at a downstream location from the pump 156. The location of the flow transmitter 160, the pump discharge pressure transmitter 158, and the temperature transmitter 162 relative to each other is arbitrary, provided the pump discharge pressure transmitter 158, the flow transmitter 160, and the temperature transmitter 162 are located in-line with one another downstream of the pump 156.

The pump suction pressure transmitter and the pump discharge pressure transmitter of one or more embodiments may be any pressure transmitter as described in FIG. 1, above. The flow transmitter of one or more embodiments may be any flow transmitter as described in FIG. 1, above. The temperature transmitter of one or more embodiments may be any pressure transmitter as described in FIG. 1, above.

The process 100 of FIG. 1 may also include a central processing unit 164. In one or more embodiments, the central processing unit 164 is in electrical communication with each of the pump suction pressure transmitter 154, the pump discharge pressure transmitter 158, the flow transmitter 160 and the temperature transmitter disposed on the liquid outlet line 146.

In one or more embodiments, the central processing unit 164 may be coupled to the degassing vessel, the pump suction pressure transmitter 154, the pump discharge pressure transmitter 158, the flow transmitter 160, and the temperature transmitter 162. The central processing unit 164 may be configured to receive and transmit any of the properties described with regard to FIG. 1, above. Electrical communication is depicted by dashed lines in FIG. 2.

The central processing unit 164 of one or more embodiments may be a computer such as the computer shown in FIG. 5. In one or more embodiments, the central processing unit 164 may also be configured to carry out methods according to one or more embodiments. The methods of one or more embodiments will be discussed in more detail in the following sections.

Keeping with FIG. 2, the gas stream **142*a* may be vented to the atmosphere and/or flared 150. In some embodiments, the gas stream 142*a* may be recycled into additional downstream processes by a gas recycle line 226. A gas flow control system 144 may be disposed on the gas outlet line 142 and may be used to control the flow of the gas stream 142*a* either to the atmosphere 150** or otherwise.

In one or more embodiments, the gas recycle line 226 may be fluidly connected to a downstream process line 214, where the downstream process line 214 is fluidly connected to an upstream side of a downstream process 206. In some embodiments, prior to entering the downstream process line 214, the gas stream **142*a* may flow through a gas compressor 248, located in-line with the gas outlet line 142. Upon flowing through the gas compressor 248, the gas stream 142*a* may be pressurized by the gas compressor 248 to produce a gas recycle stream 142*b* which is recycled to a downstream process 206 by the gas recycle line 226**.

In one or more embodiments, the reservoir 202 in FIG. 2 is located below the surface of the earth 204 and is fluidly connected to an upstream side of the degassing vessel by a reservoir line 222 entering the inlet line 138. In one or more embodiments, a reservoir inlet flow control system 224 disposed on the inlet line 138 may be used to control a flow of fluid originating from the reservoir 202. A second flow control system 236 disposed on the inlet line 138 may be used to control a portion of the fluid originating from the reservoir 202 and entering the inlet line 138.

In one or more embodiments, a first flow control system 220 may be disposed on the reservoir line 222. The first flow control system 220 may be used to control a portion of fluid originating from the reservoir 202 which may enter the downstream process line via the reservoir line 222.

In one or more embodiments, an inlet split line 232 may be fluidly connected to the inlet line 138 at a downstream side of second flow control system 236. A third flow control system 234 disposed on the inlet split line 232 may be used to control a portion of the second inlet stream (having the same composition as the second inlet stream from which it originates) which may combine with the liquid recycle stream 228 in the liquid recycle line 228 at a location upstream from the liquid recycle flow control system 230.

The reservoir inlet flow control system, the first flow control system, the second flow control system, and the third flow control system according to one or more embodiments may be include an automatic flow control valve which is configured to receive instructions related to adjust a flow rate, for example, from a computer system, and may be automatically operated to adjust the flow rate of a fluid stream according to the received instructions. In one or more embodiments, the flow control valve may be manually operated. A flow control valve may also be referred to as a flow regulator or flow controller, and these terms are to be understood according to one or more embodiments as referring to the same device. The flow control valve of one or more embodiments may include, for example, a ball valve, a check valve, a butterfly valve, a globe valve, a gate valve, a needle valve, and combinations therein. The flow transmitter of one or more embodiments may include any suitable flow ratio controller known in the art. The flow control valve may include a valve, or the flow control valve may be a flow control system, which may include both a flow control valve and a flow ratio controller and/or transmitter configured to operate the flow control valve based on instructions received from a central processing unit.

Returning to FIG. 2, in some embodiments the pressurized liquid stream **146*b* may be recycled to one or more downstream processes. For example, the pressurized liquid stream 146*b* may be recycled through a liquid recycle line 228. A liquid recycle flow control system 230 may be disposed on the liquid recycle line 228 and may be configured to control a flow of the pressurized liquid stream 146*b***.

In one or more embodiments, the liquid recycle line 228 may be fluidly connected to a downstream process line 214, where the downstream process line 214 is fluidly connected to an upstream side of a downstream process 206. The liquid recycle line 228 may be fluidly connected to the gas recycle line 226, as shown in FIG. 2, or may directly enter the downstream process line 214 (not shown).

In one or more embodiments, a reservoir fluid processing line 208 may allow for a reservoir stream 208 to flow directly into the downstream process line 214 for processing of the reservoir stream 208. A fourth flow control system 212 disposed on the reservoir fluid processing line 208 may be used to control a flow of the reservoir stream 208. The composition of the reservoir stream may be the same as the inlet stream as described above.

In one or more embodiments, a crossover line 216 may be fluidly connected to the reservoir fluid processing line 208 and may fluidly connect to the inlet line 138. A fifth flow control system 218 may be used to control a flow of a portion of the reservoir stream 208 as a crossover stream 216, allowing the crossover stream 216 to enter into the inlet line 138.

In one or more embodiments, the reservoir fluid processing line 208 may include a sixth flow control system 210 configured to control a flow of a second portion of the reservoir stream flowing through the reservoir fluid processing line 208, allowing the second portion of the reservoir stream to enter the downstream process line 214.

The crossover stream may have any components of the reservoir stream from which it originates.

The fourth, fifth, and sixth flow control systems may be any flow control system described with regard to the reservoir flow control system, above.

Figure 3:
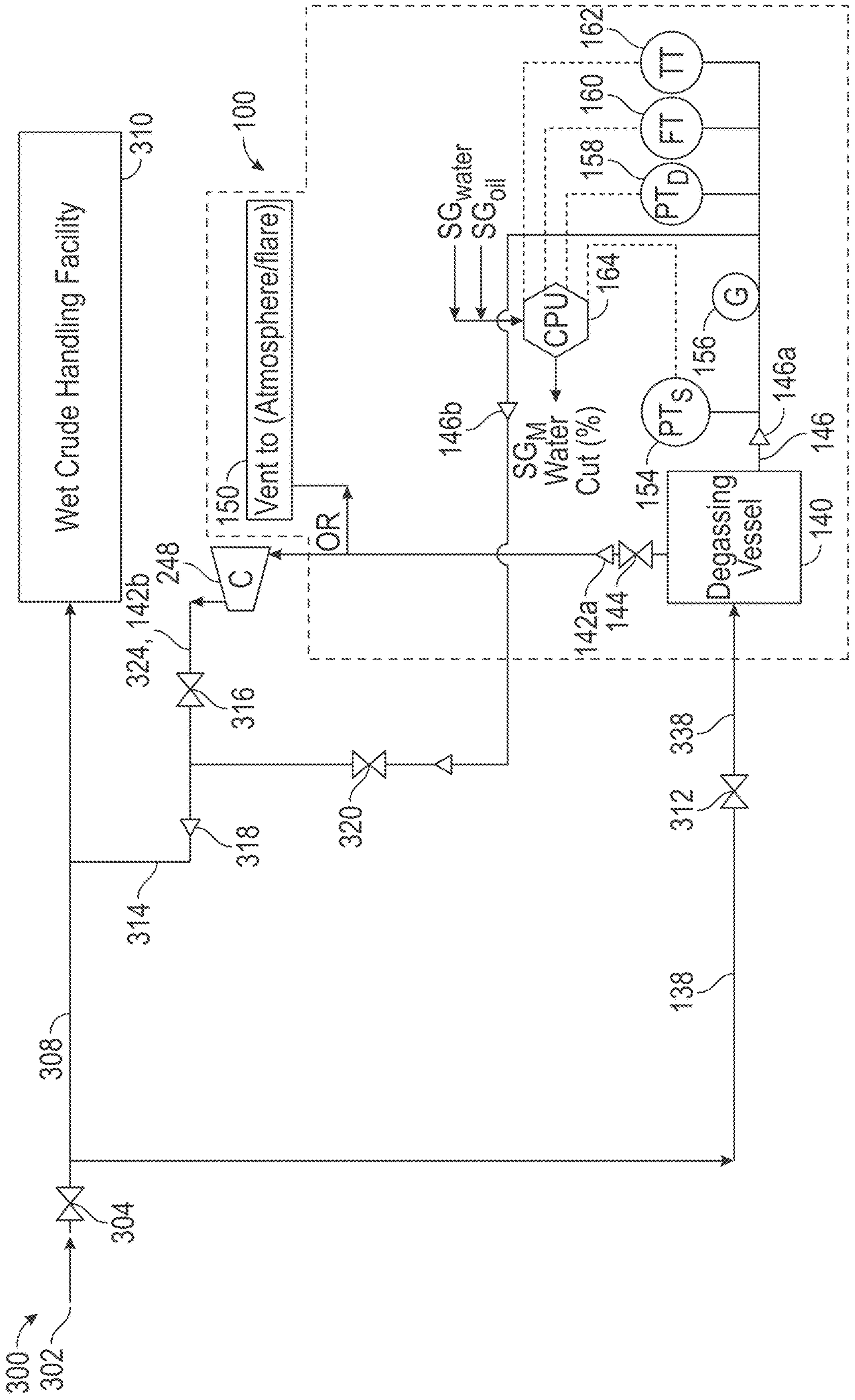
FIG. 3 illustrates a second system for determining water cut according to one or more embodiments.

FIG. 3 shows a second system 300 according to one or more embodiments. The second system 300 shown in FIG. 3 includes the process 100 of FIG. 1 applied to a wet crude handling facility. The second system 300 may include the process 100 of FIG. 1, a wet crude handling facility 310, and an upstream process 302.

In one or more embodiments, the second system 300 includes the process 100 of FIG. 1, including all of the elements as described with regard to FIG. 1 and FIG. 2, above. For the sake of brevity, the process 100 of FIG. 1 will not be described again here.

The third inlet stream 338 in FIG. 3 may originate from an upstream process 302. Accordingly, the third inlet stream 338 may contain any components associated with an oil and gas reservoir including but not limited to oil and other hydrocarbons, water, natural gas and other dissolved gases including but not limited to hydrogen sulfide ($H_2S$) and carbon dioxide ($CO_2$), dissolved solids, and the like. As would be understood by one of ordinary skill in the art, compositions of the third inlet stream 338 may vary based on many factors including geological location, reservoir characteristics (rock types, temperatures, depths, pressure), and the like. However, the third inlet stream 338 in the second system 300 of one or more embodiments may contain primarily oil, water, and gas in compositions those described with regard to FIG. 1, above.

Keeping with FIG. 3, a gas stream **142*a* separated by the degassing vessel 140 (described in more detail, above) may be vented to the atmosphere and/or flared 150. In some embodiments, the gas stream 142*a* may be recycled into additional upstream processes by a gas recycle line 324. In one or more embodiments, the gas recycle line 324 may be fluidly connected to a recycle line 314 and an upstream process line 308, where the upstream process line 308 may be fluidly connected an upstream process 302 and to an upstream side of another process, such as a wet crude handling facility 310**.

In some embodiments, prior to entering the upstream process line 308, the gas stream **142*a* may flow through a gas compressor 248, located in-line with the gas outlet line 142. Upon flowing through the gas compressor 248, the gas stream 142*a* may be pressurized by the gas compressor 248 to produce a gas recycle stream 142*b* which is recycled to the wet crude handling facility 310 by the gas recycle line 324**.

In one or more embodiments, the upstream process 302 is fluidly connected to an upstream side of the degassing vessel by the inlet line 138. In one or more embodiments, an inlet flow control system 312 disposed on the inlet line 138 may be used to control a flow of fluid.

The inlet flow control system according to one or more embodiments may be include an automatic flow control valve which is configured to receive instructions related to adjust a flow rate, for example, from a computer system, and may be automatically operated to adjust the flow rate of a fluid stream according to the received instructions. In one or more embodiments, the flow control valve may be manually operated. A flow control valve may also be referred to as a flow regulator or flow controller, and these terms are to be understood according to one or more embodiments as referring to the same device. The flow control valve of one or more embodiments may include, for example, a ball valve, a check valve, a butterfly valve, a globe valve, a gate valve, a needle valve, and combinations therein. The flow transmitter of one or more embodiments may include any suitable flow ratio controller known in the art. The flow control valve may include a valve, or the flow control valve may be a flow control system, which may include both a flow control valve and a flow ratio controller and/or transmitter configured to operate the flow control valve based on instructions received from a central processing unit.

Returning to FIG. 3, in some embodiments the pressurized liquid stream **146*b* may also be recycled to one or more processes such as the wet crude handling facility 310. For example, the pressurized liquid stream 146*b* may be recycled through a liquid recycle line 318. A liquid recycle flow control system 320 may be disposed on the liquid recycle line 318 and may be configured to control a flow of the pressurized liquid stream 146*b***.

In one or more embodiments, the liquid recycle line 318 may be fluidly connected to the recycle line 314 and the upstream process line 308. The liquid recycle line 318 may be fluidly connected to the recycle line 314, as shown in FIG. 3, or may directly enter the upstream process line 308 (not shown).

In one or more embodiments, an upstream mixture stream 302 may flow directly into the upstream process line 308 for processing of the upstream mixture stream 302. An upstream flow control system 304 disposed on the upstream process line 308 may be used to control a flow of the upstream mixture stream 302.

The composition of the upstream mixture stream may be the same as the inlet stream as described above.

The upstream flow control system may be any flow control system described with regard to the inlet flow control system, above.

Method for Determining Water Cut

Figure 4:
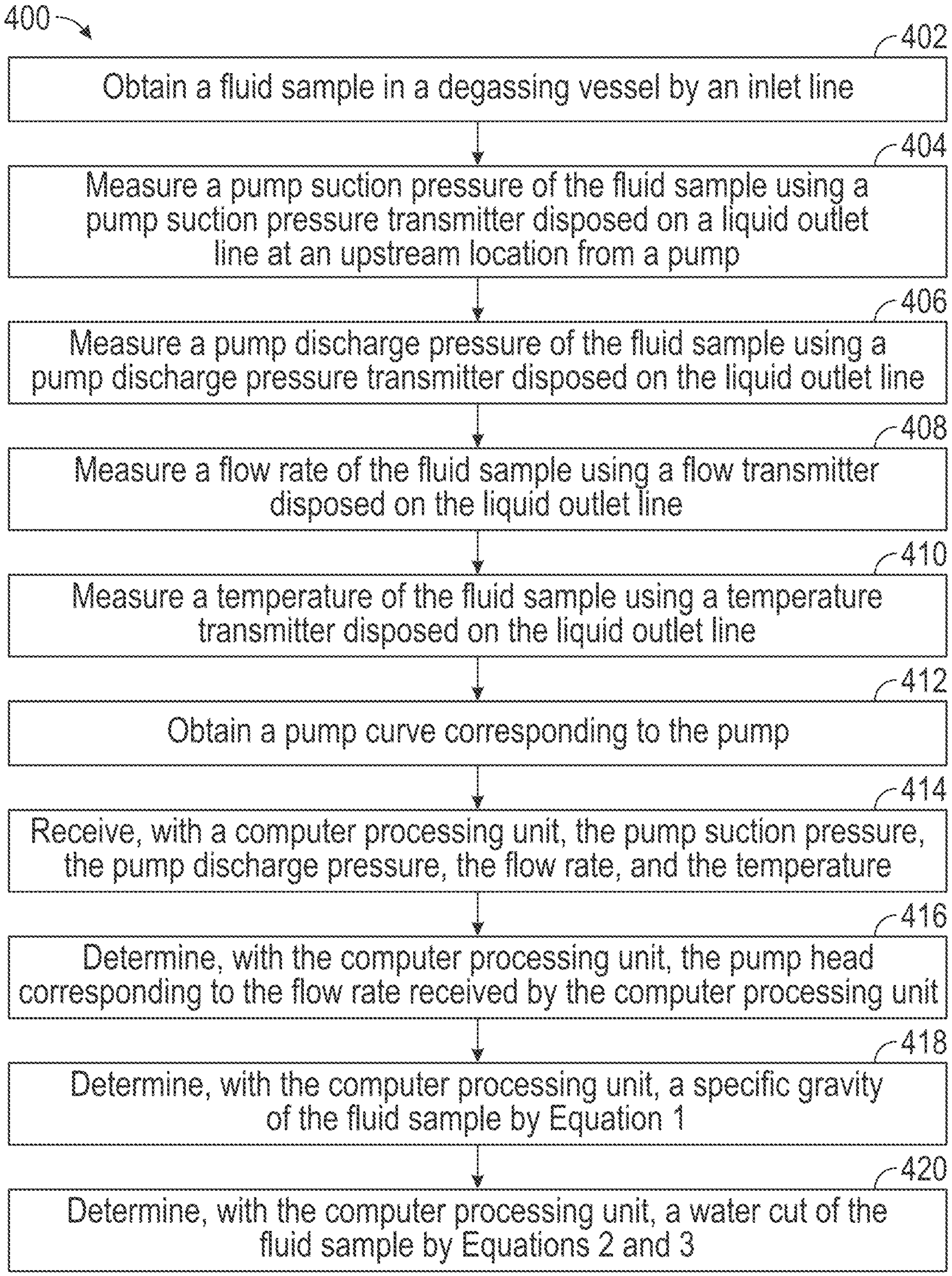
FIG. 4 is a flowchart of a method for determining water cut according to one or more embodiments.

Embodiments disclosed herein also relate to methods for determining water cut. FIG. 4 shows an example method 400 according to one or more embodiments disclosed herein.

The method 400 includes, in step 402, obtaining a fluid sample in a degassing vessel by an inlet line, fluidly connected to and entering the degassing vessel. In step 404, the method 400 further includes a pump suction pressure of the fluid sample using a pump suction pressure transmitter disposed on a liquid outlet line at an upstream location from a pump. In step 406, the method 400 further includes measuring a pump discharge pressure of the fluid sample using a pump discharge pressure transmitter disposed on the liquid outlet line. The method 400 also includes, in step 408, measuring a flow rate of the fluid sample using a flow transmitter disposed on the liquid outlet line and in step 410, measuring a temperature of the fluid sample using a temperature transmitter disposed on the liquid outlet line. As shown in the process and systems described in FIGS. 1-3, the inlet line may fluidly connect to and enter the degassing vessel, the pump suction pressure transmitter may be disposed on a liquid outlet line at an upstream location from a pump, and the liquid outlet line may be fluidly connected with and exiting the degassing vessel. As also described in the previous Figures, the pump discharge pressure transmitter, the flow transmitter, and the temperature transmitter may be disposed on the liquid outlet line in-line with each other, at a downstream location from the pump.

The method 400 also includes, in step 412 obtaining a pump curve corresponding to the pump. As described in sections above, the pump curve is defined as a relationship between the flow rate and a pump head.

In step 414 of the method 400, the pump suction pressure, the pump discharge pressure, the flow rate, and the temperature may be received with a computer processing unit. The computer processing unit is coupled to the degassing vessel, the pump suction pressure transmitter, the pump discharge pressure transmitter, the flow transmitter, and the temperature transmitter. The Central Processing Unit (Computer) which is connected to the pump will receive the operating parameter ($P_s$, $P_d$, T and Q). In some embodiments, the specific gravity for each liquid ($SG_{oil}$ and $SG_{water}$) will be defined and configured. The pump performance curve is uploaded and saved inside the CPU for the calculations.

The method 400 also includes, in step 416, determining, with the computer processing unit, the pump head corresponding to the flow rate received by the computer processing unit.

The method 400 further includes, in step 418, determining, with the computer processing unit, a specific gravity of the fluid sample by Equation 1:

$$SG_{Mixture} = \frac{(P_d - P_s) * 2.31}{H} \quad \text{(Equation 1)}$$

where $SG_{Mixture}$ is the specific gravity of the fluid sample, $P_d$ is the pump discharge pressure, $P_s$ is the pump suction pressure, and H is the pump head.

Additionally, the method 400 includes, in step 420, determining, with the computer processing unit, a water cut of the fluid sample by Equations 2 and 3:

$$y_{water} = \frac{SG_{Mixture} - SG_{Oil}}{SG_{Water} - SG_{Oil}} \quad \text{(Equation 2)}$$

$$\%_{WaterCut} = y_{water} \times 100 \quad \text{(Equation 3)}$$

where $y_{water}$ is a volume fraction of water, $SG_{Oil}$ is a specific gravity of oil in the fluid sample, and $SG_{Water}$ is a specific gravity of water in the fluid sample.

In some embodiments, the method further includes correcting the calculated specific gravity ($SG_{Mixture}$) for temperature variations. The temperature corrected specific gravity of the fluid sample is then determined, with the computer processing unit, by Equation 4:

$$SG_M = SG_{Mixture} + [3.31 \times 10^{-4} \times (T(°\text{F}) - 60)] \quad \text{(Equation 4)}$$

where $SG_M$ is the temperature corrected specific gravity of the fluid sample, $SG_{Mixture}$ is the specific gravity of the fluid sample determined from Equation 1, and T is temperature of the fluid sample in degrees Fahrenheit.

In some embodiments, the method further includes determining, with the computer processing unit, a temperature corrected water cut of the fluid sample by Equations 5 and 6:

$$y_{water,T} = \frac{SG_M - SG_{Oil}}{SG_{Water} - SG_{Oil}} \quad \text{(Equation 5)}$$

$$\%_{WaterCut,T} = y_{water,T} \times 100 \quad \text{(Equation 6)}$$

where $y_{water,T}$ is a volume fraction of water, $SG_M$ is the temperature corrected specific gravity of the fluid sample, $SG_{Oil}$ is a specific gravity of oil in the fluid sample, and $SG_{Water}$ is a specific gravity of water in the fluid sample.

FIG. 5 shows a computer 500 system that may be used in the control process for adjusting a temperature to minimize fuel consumption in an incinerator system in accordance with one or more embodiments. Specifically, FIG. 5 shows a block diagram of a computer 500 system used to provide computational functionalities associated with described algorithms, methods, functions, processes, flows, and procedures as described in the instant disclosure, according to an implementation. The illustrated computer 500 is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device.

Additionally, the computer 500 may include a computer that includes an input device, such as a keypad, keyboard, touch screen, or other device that can accept user information, and an output device that conveys information associated with the operation of the computer 500, including digital data, visual, or audio information (or a combination of information), or a GUI.

The computer 500 can serve in a role as a client, network component, a server, a database or other persistency, or any other component (or a combination of roles) of a computer system for performing the subject matter described in the instant disclosure. The illustrated computer 500 is communicably coupled with a network 502. In some implementations, one or more components of the computer 500 may be configured to operate within environments, including cloud-computing-based, local, global, or other environment (or a combination of environments).

At a high level, the computer 500 is an electronic computing device operable to receive, transmit, process, store, or manage data and information associated with the described subject matter. According to some implementations, the computer 500 may also include or be communicably coupled with an application server, e-mail server, web server, caching server, streaming data server, business intelligence (BI) server, or other server (or a combination of servers).

The computer 500 can receive requests over network 502 from a client application (for example, executing on another computer 500) and responding to the received requests by processing the said requests in an appropriate software application. In addition, requests may also be sent to the computer 500 from internal users (for example, from a command console or by other appropriate access method), external or third-parties, other automated applications, as well as any other appropriate entities, individuals, systems, or computers.

Each of the components of the computer 500 can communicate using a system bus 504. In some implementations, any or all of the components of the computer 500, both hardware or software (or a combination of hardware and software), may interface with each other or the interface 506 (or a combination of both) over the system bus 504 using an application programming interface (API) 508 or a service layer 510 (or a combination of the API 508 and service layer 510. The API 508 may include specifications for routines, data structures, and object classes. The API 508 may be either computer-language independent or dependent and refer to a complete interface, a single function, or even a set of APIs. The service layer 510 provides software services to the computer 500 or other components (whether or not illustrated) that are communicably coupled to the computer 500.

The functionality of the computer 500 may be accessible for all service consumers using this service layer 510. Software services, such as those provided by the service layer 510, provide reusable, defined business functionalities through a defined interface. For example, the interface may be software written in JAVA, C++, or other suitable language providing data in extensible markup language (XML) format or other suitable format. While illustrated as an integrated component of the computer 500, alternative implementations may illustrate the API 508 or the service layer 510 as stand-alone components in relation to other components of the computer 500 or other components (whether or not illustrated) that are communicably coupled to the computer 500. Moreover, any or all parts of the API 508 or the service layer 510 may be implemented as child or sub-modules of another software module, enterprise application, or hardware module without departing from the scope of this disclosure.

The computer 500 includes an interface 506. Although illustrated as a single interface 506 in FIG. 5, two or more interfaces 506 may be used according to particular needs, desires, or particular implementations of the computer 500. The interface 506 is used by the computer 500 for communicating with other systems in a distributed environment that are connected to the network 502. Generally, the interface 506 includes logic encoded in software or hardware (or a combination of software and hardware) and operable to communicate with the network 502. More specifically, the interface 506 may include software supporting one or more communication protocols associated with communications such that the network 502 or interface's hardware is operable to communicate physical signals within and outside of the illustrated computer 500.

The computer 500 includes at least one computer processor 512. Although illustrated as a single computer processor 512 in FIG. 5, two or more processors may be used according to particular needs, desires, or particular implementations of the computer 500. Generally, the computer processor 512 executes instructions and manipulates data to perform the operations of the computer 500 and any algorithms, methods, functions, processes, flows, and procedures as described in the instant disclosure.

The computer 500 also includes a non-transitory computer 500 readable medium, or a memory 514, that holds data for the computer 500 or other components (or a combination of both) that can be connected to the network 502. For example, memory 514 can be a database storing data consistent with this disclosure. Although illustrated as a single memory 514 in FIG. 5, two or more memories may be used according to particular needs, desires, or particular implementations of the computer 500 and the described functionality. While memory 514 is illustrated as an integral component of the computer 500, in alternative implementations, memory 514 can be external to the computer 500.

The application 516 is an algorithmic software engine providing functionality according to particular needs, desires, or particular implementations of the computer 500, particularly with respect to functionality described in this disclosure. For example, application 516 can serve as one or more components, modules, applications, etc. Further, although illustrated as a single application 516, the application 516 may be implemented as multiple applications 516 on the computer 500. In addition, although illustrated as integral to the computer 500, in alternative implementations, the application 516 can be external to the computer 500.

There may be any number of computers 500 associated with, or external to, a computer system containing computer 500, each computer 500 communicating over network 502. Further, the term "client," "user," and other appropriate terminology may be used interchangeably as appropriate without departing from the scope of this disclosure. Moreover, this disclosure contemplates that many users may use one computer 500, or that one user may use multiple computers 500.

FIG. 6 shows an example pump curve 600 according to one or more embodiments. The pump curve 600 may provide a relationship between two or more different performance factors of a pump on the y-axis in relation to a flow rate of fluid passing through the pump, depicted on the x-axis. In the example pump curve 600 shown in FIG. 6, the performance factors are pump head (ft) on the left-hand side y-axis, and efficiency and power (%) on the right-hand side y-axis. Plotted on the example pump curve 600 are the pump head capacity (H-Q), pump brake horsepower (BHP), and efficiency (n). Head capacity graphically expresses how much flow (Q) can be generated due to the increased head (H) (pressure), which is added to the fluid by the pump. Brake horsepower indicates the horsepower required to operate a pump at a given point on the performance curve. The efficiency curve shows how efficient the pump will operate at a give flowrate.

Embodiments disclosed herein may provide at least one of the following advantages.

Embodiments disclosed herein may be advantageously used in various field applications such as subsea reservoirs and wet crude handling facilities, or any suitable application where water cut needs to be determined.

Embodiments disclosed herein may be used to calculate the water cut directly from available process parameters. Thus, providing reliable and accurate water cut values compared to the complex water cut meters available in the market.

One or more embodiments disclosed herein provides an approach to identify the water cut utilizing the pump performance curve data and calculation. The described embodiments may have longer lifetime and calibration duration compared to the existing systems. Furthermore, systems and methods according to embodiments described herein may be more accurate, simpler, and have lower capital and maintenance costs compared to the existing or conventional systems. In contrast to embodiments disclosed herein, existing design of density meters works on multiple sensors or oscillator which measure the frequency as the material composition changes.

What is claimed:

1. A process for determining water cut of a fluid sample in an oil and gas process facility, comprising:

a degassing vessel, the degassing vessel comprising, an inlet line, fluidly connected to and entering the degassing vessel, a gas outlet line and a liquid outlet line, both fluidly connected to and exiting the degassing vessel, a pump suction pressure transmitter disposed on the liquid outlet line configured to measure a pump suction pressure, a pump discharge pressure transmitter disposed on the liquid outlet line configured to measure a pump discharge pressure, a flow transmitter disposed on the liquid outlet line configured to measure a flow rate, and a temperature transmitter, configured to measure a temperature, disposed on the liquid outlet line;

a pump fluidly connected to the degassing vessel via the liquid outlet line; and a computer processing unit, coupled to the degassing vessel, the pump suction pressure transmitter, the pump discharge pressure transmitter, the flow transmitter, and the temperature transmitter, the computer processing unit having a memory and processor, the memory storing instructions that, when executed by the processor, cause the processor to:

measure:

the pump suction pressure of the fluid sample in the degassing vessel, the pump discharge pressure of the fluid sample, the flow rate of the fluid sample, and the temperature of the fluid sample, obtain a pump curve corresponding to the pump, the pump curve comprising a relationship between the flow rate and a pump head;

receive the pump suction pressure, the pump discharge pressure, the flow rate, and the temperature;

determine the pump head corresponding to the flow rate received by the computer processing unit;

determine a specific gravity of the fluid sample by Equation 1:

$$SG_{Mixture} = \frac{(P_d - P_s) * 2.31}{H} \quad \text{(Equation 1)}$$

where $SG_{Mixture}$ is the specific gravity of the fluid sample, $P_d$ is the pump discharge pressure, $P_s$ is the pump suction pressure, and H is the pump head; and determine a water cut of the fluid sample by Equations 2 and 3:

$$y_{water} = \frac{SG_{Mixture} - SG_{Oil}}{SG_{Water} - SG_{Oil}} \quad \text{(Equation 2)}$$

$$\%_{WaterCut} = y_{water} \times 100 \quad \text{(Equation 3)}$$

where $y_{water}$ is a volume fraction of water, $SG_{Oil}$ is a specific gravity of oil in the fluid sample, and $SG_{Water}$ is a specific gravity of water in the fluid sample.

2. The process of claim 1, wherein the degassing vessel is configured to receive an inlet stream flowing in the inlet line and separate the inlet stream into a liquid stream and a gas stream, wherein the liquid stream flows through the liquid outlet line and the gas stream flows through the gas outlet line.

3. The process of claim 2, wherein the pump is configured to pressurize the liquid stream flowing through the liquid outlet line to produce a pressurized liquid stream.

4. The process of claim 1, further comprising a gas flow control system disposed on the gas outlet line and configured to control a flow of a gas exiting the degassing vessel.

5. The process of claim 1, wherein the pump suction pressure transmitter is located at an upstream location from the pump, and the pump discharge pressure transmitter is located at a downstream location from the pump and wherein the flow transmitter and the temperature transmitter are located in-line with the pump discharge pressure transmitter at a downstream location from the pump.

6. The process of claim 1, wherein the pump is a centrifugal pump.

7. The process of claim 1, wherein the computer processing unit is further configured to:

determine a temperature corrected specific gravity of the fluid sample by Equation 4:

$$SG_M = SG_{Mixture} + \left[3.31 \times 10^{-4} \times (T(^{\circ}\mathrm{F}) - 60)\right] \quad \text{(Equation 4)}$$

where $SG_M$ is the temperature corrected specific gravity of the fluid sample, $SG_{Mixture}$ is the specific gravity of the fluid sample determined from Equation 1, and T is temperature of the fluid sample in degrees Fahrenheit.

8. The process of claim 7, wherein the computer processing unit is further configured to:

determine a temperature corrected water cut of the fluid sample by Equations 5 and 6:

$$y_{water,T} = \frac{SG_M - SG_{Oil}}{SG_{Water} - SG_{Oil}} \quad \text{(Equation 5)}$$

$$\%_{WaterCut,T} = y_{water,T} \times 100 \quad \text{(Equation 6)}$$

where $y_{water,T}$ is a volume fraction of water, $SG_M$ is the temperature corrected specific gravity of the fluid sample, $SG_{Oil}$ is a specific gravity of oil in the fluid sample, and $SG_{Water}$ is a specific gravity of water in the fluid sample.

9. A method for determining water cut of a fluid sample in an oil and gas process facility, comprising:

obtaining the fluid sample in a degassing vessel by an inlet line, fluidly connected to and entering the degassing vessel;

measuring a pump suction pressure of the fluid sample using a pump suction pressure transmitter disposed on a liquid outlet line at an upstream location from a pump;

measuring a pump discharge pressure of the fluid sample using a pump discharge pressure transmitter disposed on the liquid outlet line;

measuring a flow rate of the fluid sample using a flow transmitter disposed on the liquid outlet line; and measuring a temperature of the fluid sample using a temperature transmitter disposed on the liquid outlet line;

wherein the liquid outlet line is fluidly connected with and exiting the degassing vessel, and wherein the pump discharge pressure transmitter, the flow transmitter, and the temperature transmitter in-line with each other at a downstream location from the pump;

obtaining a pump curve corresponding to the pump, the pump curve comprising a relationship between the flow rate and a pump head;

receiving, with a computer processing unit, the pump suction pressure, the pump discharge pressure, the flow rate, and the temperature, wherein the computer processing unit is coupled to the degassing vessel, the pump suction pressure transmitter, the pump discharge pressure transmitter, the flow transmitter, and the temperature transmitter;

determining, with the computer processing unit, the pump head corresponding to the flow rate received by the computer processing unit;

determining, with the computer processing unit, a specific gravity of the fluid sample by Equation 1:

$$SG_{Mixture} = \frac{(P_d - P_s) * 2.31}{H} \quad \text{(Equation 1)}$$

where $SG_{Mixture}$ is the specific gravity of the fluid sample, $P_d$ is the pump discharge pressure, $P_s$ is the pump suction pressure, and H is the pump head; and determining, with the computer processing unit, a water cut of the fluid sample by Equations 2 and 3:

$$y_{water} = \frac{SG_{Mixture} - SG_{Oil}}{SG_{Water} - SG_{Oil}} \quad \text{(Equation 2)}$$

$$\%_{WaterCut} = y_{water} \times 100 \quad \text{(Equation 3)}$$

where $y_{water}$ is a volume fraction of water, $SG_{Oil}$ is a specific gravity of oil in the fluid sample, and $SG_{Water}$ is a specific gravity of water in the fluid sample.

10. The method of claim 9, further comprising:

determining, with the computer processing unit, a temperature corrected specific gravity of the fluid sample by Equation 4:

$$SG_M = SG_{Mixture} + [3.31 \times 10^{-4} \times (T(°F) - 60)] \quad \text{(Equation 4)}$$

where $SG_M$ is the temperature corrected specific gravity of the fluid sample, $SG_{Mixture}$ is the specific gravity of the fluid sample determined from Equation 1, and T is temperature of the fluid sample in degrees Fahrenheit.

11. The method of claim 10, further comprising:

determining, with the computer processing unit, a temperature corrected water cut of the fluid sample by Equations 5 and 6:

$$y_{water,T} = \frac{SG_M - SG_{Oil}}{SG_{Water} - SG_{Oil}} \quad \text{(Equation 5)}$$

$$\%_{WaterCut,T} = y_{water,T} \times 100 \quad \text{(Equation 6)}$$

where $y_{water}$, T is a volume fraction of water, $SG_M$ is the temperature corrected specific gravity of the fluid sample, $SG_{Oil}$ is a specific gravity of oil in the fluid sample, and $SG_{Water}$ is a specific gravity of water in the fluid sample.

12. A system for determining water cut of a fluid sample in an oil and gas process facility, comprising:

a degassing vessel, the degassing vessel comprising, an inlet line, fluidly connected to and entering the degassing vessel, a gas outlet line and a liquid outlet line, both fluidly connected to and exiting the degassing vessel, a pump suction pressure transmitter disposed on the liquid outlet line configured to measure a pump suction pressure, a pump discharge pressure transmitter disposed on the liquid outlet line configured to measure a pump discharge pressure, a flow transmitter disposed on the liquid outlet line configured to measure a flow rate, and a temperature transmitter disposed on the liquid outlet line configured to measure a temperature;

a pump, fluidly connected to the degassing vessel via the liquid outlet line;

a reservoir fluidly connected to an upstream side of the degassing vessel by the inlet line;

a downstream process line fluidly connected to a downstream side of the degassing vessel and to the reservoir; and a computer processing unit, coupled to the degassing vessel, the pump suction pressure transmitter, the pump discharge pressure transmitter, the flow transmitter, and the temperature transmitter, the computer processing unit having a memory and processor, the memory storing instructions that, when executed by the processor, cause the processor to:

measure the pump suction pressure of the fluid sample in the degassing vessel;

measure the pump discharge pressure of the fluid sample;

measure the flow rate of the fluid sample;

measure the temperature of the fluid sample;

obtain a pump curve corresponding to the pump, the pump curve comprising a relationship between the flow rate and a pump head;

receive the pump suction pressure, the pump discharge pressure, the flow rate, and the temperature;

determine the pump head corresponding to the flow rate received by the computer processing unit;

determine a specific gravity of the fluid sample by Equation 1:

$$SG_{Mixture} = \frac{(P_d - P_s) * 2.31}{H} \quad \text{(Equation 1)}$$

where $SG_{Mixture}$ is the specific gravity of the fluid sample, $P_d$ is the pump discharge pressure, $P_s$ is the pump suction pressure, and H is the pump head; and determine a water cut of the fluid sample by Equations 2 and 3:

$$y_{water} = \frac{SG_{Mixture} - SG_{Oil}}{SG_{Water} - SG_{Oil}} \quad \text{(Equation 2)}$$

-continued $$\%_{WaterCut} = y_{water} \times 100 \quad \text{(Equation 3)}$$

where $y_{water}$ is a volume fraction of water, $SG_{Oil}$ is a specific gravity of oil in the fluid sample, and $SG_{Water}$ is a specific gravity of water in the fluid sample.

13. The system of claim 12, further comprising a gas flow control system disposed on the gas outlet line and configured to control a flow of a gas exiting the degassing vessel.

14. The system of claim 13, further comprising:

a gas compressor fluidly connected to the degassing vessel by the gas outlet line and located downstream of the gas flow control system; and a gas recycle line comprising a gas recycle flow control system fluidly connected to the downstream process line and to a downstream side of the gas compressor.

15. The system of claim 12, wherein the pump suction pressure transmitter is located at an upstream location from the pump, and the pump discharge pressure transmitter is located at a downstream location from the pump.

16. The system of claim 15, wherein the flow transmitter and the temperature transmitter are located in-line with the pump discharge pressure transmitter at a downstream location from the pump.

17. The system of claim 12, wherein the pump is a centrifugal pump.

18. The system of claim 12, wherein the liquid outlet line is fluidly connected to a liquid recycle line and the liquid recycle line is fluidly connected to the downstream process line, wherein a liquid recycle flow control system is disposed on the liquid recycle line.

19. The system of claim 12, wherein the computer processing unit is further configured to:

determine a temperature corrected specific gravity of the fluid sample by Equation 4:

$$SG_M = SG_{Mixture} + \left[3.31 \times 10^{-4} \times (T(°\text{F}) - 60)\right] \quad \text{(Equation 4)}$$

where $SG_M$ is the temperature corrected specific gravity of the fluid sample, $SG_{Mixture}$ is the specific gravity of the fluid sample determined from Equation 1, and T is temperature of the fluid sample in degrees Fahrenheit.

20. The system of claim 19, wherein the computer processing unit is further configured to:

determine a temperature corrected water cut of the fluid sample by Equations 5 and 6:

$$y_{water,T} = \frac{SG_M - SG_{Oil}}{SG_{Water} - SG_{Oil}} \quad \text{(Equation 5)}$$

$$\%_{WaterCut,T} = y_{water,T} \times 100 \quad \text{(Equation 6)}$$

where $y_{water,T}$ is a volume fraction of water, $SG_M$ is the temperature corrected specific gravity of the fluid sample, $SG_{Oil}$ is a specific gravity of oil in the fluid sample, and $SG_{Water}$ is a specific gravity of water in the fluid sample.

* * * * *